US009168125B2

(12) United States Patent
Jorcano Noval et al.

(10) Patent No.: US 9,168,125 B2
(45) Date of Patent: Oct. 27, 2015

(54) ARTIFICIAL DERMIS AND METHOD OF PREPARATION

(75) Inventors: Jose Luis Jorcano Noval, Madrid (ES); Fernando Larcher Laguzzi, Madrid (ES); Alvaro Meana Infiesta, Asturias (ES); Sara Gomez Llanes, Asturias (ES); Marcela Del Rio Nechaevsky, Madrid (ES)

(73) Assignees: Centro De Investigaciones Energeticas Medioambientales Y Tecnologicas, Madrid (ES); Centro Comunitario De Transfusion De Asturias-cruz Roja Espanola, Oviedo (ES); Fundacion Marcelino Botin, Santander (ES)

( * ) Notice: Subject to any disclaimer, the term of this patent is extended or adjusted under 35 U.S.C. 154(b) by 82 days.

(21) Appl. No.: 13/367,548

(22) Filed: Feb. 7, 2012

(65) Prior Publication Data

US 2012/0183505 A1 Jul. 19, 2012

Related U.S. Application Data

(63) Continuation of application No. 11/809,665, filed on May 31, 2007, now abandoned, which is a continuation of application No. 10/469,554, filed as application No. PCT/ES02/00087 on Feb. 28, 2002, now Pat. No. 7,244,552.

(30) Foreign Application Priority Data

Mar. 1, 2001 (ES) .................................. 200100494

(51) Int. Cl.
*A61F 2/10* (2006.01)
*A61L 27/60* (2006.01)
(Continued)

(52) U.S. Cl.
CPC .................. *A61F 2/105* (2013.01); *A61K 35/33* (2013.01); *A61K 35/36* (2013.01); *A61L 27/60* (2013.01)

(58) Field of Classification Search
None
See application file for complete search history.

(56) References Cited

U.S. PATENT DOCUMENTS 4,485,096 A 11/1984 Bell
5,318,782 A 6/1994 Weis-Fogh
(Continued)

FOREIGN PATENT DOCUMENTS

EP 0 373 044 6/1990
ES 2 117 573 8/1998
(Continued)

OTHER PUBLICATIONS

PCT International Search Report (mailing date: Apr. 9, 2002) for PCT Application No. PCT/ES02/00087 ( 2 pages).
(Continued)

*Primary Examiner* — Allison Fox
(74) *Attorney, Agent, or Firm* — Ladas & Parry LLP

(57) ABSTRACT

Artificial dermis (1) obtained from plasma with platelets (2) and human fibroblasts. The plasma with platelets (2) is obtained from the fractionating of total blood (4) from the patient (8) by light centrifugation, and the human fibroblasts (3) from a skin biopsy, (5). Clotting is obtained by adding calcium. This artificial dermis (1) permits rapid growth of the keratinocytes (6) seeded on its surface to build an artificial skin (7) which can easily be transplanted. Large areas of artificial dermis (1) are obtained from small amounts of starting materials and can be enriched with cytokines and platelet growth factors, to strengthen proliferation of the cells seeded. The artificial skin (7) obtained can be used to treat major burn treatments, chronic skin ulcers, etc., or be used, by employing genetically altered cells, as a vehicle for gene therapy.

9 Claims, 1 Drawing Sheet

(51) Int. Cl.
A61K 35/33 (2015.01)
A61K 35/36 (2015.01)

(56) References Cited

U.S. PATENT DOCUMENTS 5,733,545 A 3/1998 Hood, III
2003/0166274 A1* 9/2003 Hewitt et al. ............... 435/366
2006/0240555 A1 10/2006 Ronfard

FOREIGN PATENT DOCUMENTS

ES 2 132 027 8/1999
JP 10-277143 10/1998

OTHER PUBLICATIONS

Abstract ( 1 page) of Anitua, E., "Plasma Rich in Growth Factors: Preliminary Results of Use in the Preparation of Future Sites for Implants," Int J Oral Maxillofac Implants, vol. 14, No. 4, pp. 529-535 (1999).
Abstract ( 1 page) of Boyce, S.T., et al., "Biologic Attachment, Growth, and Differentiation of Cultured Human Epidermal Keratinocytes on a Graftable Collagen and Chondroitin-6-Sulfate Substrate," Surgery, vol. 103, No. 4, pp. 421-431 (Apr. 1988).
Abstract ( 1 page) of Giardino R., et al., "Polylactide Bioabsorbable Polymers for Guided Tissue Regeneration," J Trauma, vol. 47, No. 2, pp. 303-308 (Aug. 1999).
Abstract ( 1 page) of Martin, P., "Wound Healing-Aiming for Perfect Skin Regeneration," Science, vol. 276, No. 5309, pp. 75-81 (Apr. 4, 1997).
Abstract ( 1 page) of Meana, A., et al., "Large Surface of Cultured Human Epithelium Obtained on a Dermal Matrix Based on Fibroblast-Containing Fibrin Gels," Burns I vol. 24, No. 7, pp. 621-630 (Nov. 1998).
Abstract ( 1 page) of Muhart, M., et al., "Behavior of Tissue-Engineered Skin: Equivalent, Autograft, and Oclusive Dressing in Human Donor Sites," Arch Dermatol, vol. 135, No. 8, pp. 913-918 (Aug. 1999).
Abstract ( 1 page) of Myers, G.A., "Management of Paraesophageal Hernia with a Selective Approach to Antoreflux Surgery," Am J Surg, vol. I 70, No. 4, pp. 375-380 (Oct. 1995).
Abstract ( 1 page) of Navasaria, H.A., et al., "Culturing Skin in vitro for Wound Therapy," Trends Biotechnol, vol. 13, No. 3, pp. 91-100 (Mar. 1995).
Abstract ( 1 page) of Naughton, G.K., et al., "Human-Based Tissue-Engineered Implants for Plastic and Reconstructive Surgery," Clin Plast Surg. vol. 26, No. 4,pp. 579-586, viii (Oct. 1999).
Abstract ( 1 page) of Pellegrini, G., et al., "The Control of Epidermal Stem Cells (Holoclones) in the Treatment of Massive Full-Thickness Burns with Autologous Keratinocytes Cultured on Fibrin," Transplantation, vol. 68, No. 6, pp. 868-879 (Sep. 27, 1999).
Abstract ( 1 page) of Ronfard, V., et al., "Use of Human Keratinocytes Cultured on Fibrin Glue in the Treatment of Burn Wounds," Burns I vol. 17, No. 3, pp. 181-184 (Jun. 1991).
Abstract ( 1 page) of Stark G.B., et al, "Cologne Burn Centre Experience with Glycerol-Preserved Allogeneic Skin: Part II: Combination with Autologous Cultured Keratinocytes," Burns I vol. 20, Suppl. 1, pp. S34-S38 (1994).
Jockusch et al., Proceedings of the National Academy of Sciences, USA, 1996, vol. 93, pp. 7446-7451.
Whitman et al., "Platelet Gel: An Autologous Alternative to Fibrin Glue With Applications in Oral and Maxillofacial Surgery" J Oral Maxillofac Surg. 1997, vol. 55, p. 1294-1299.

* cited by examiner

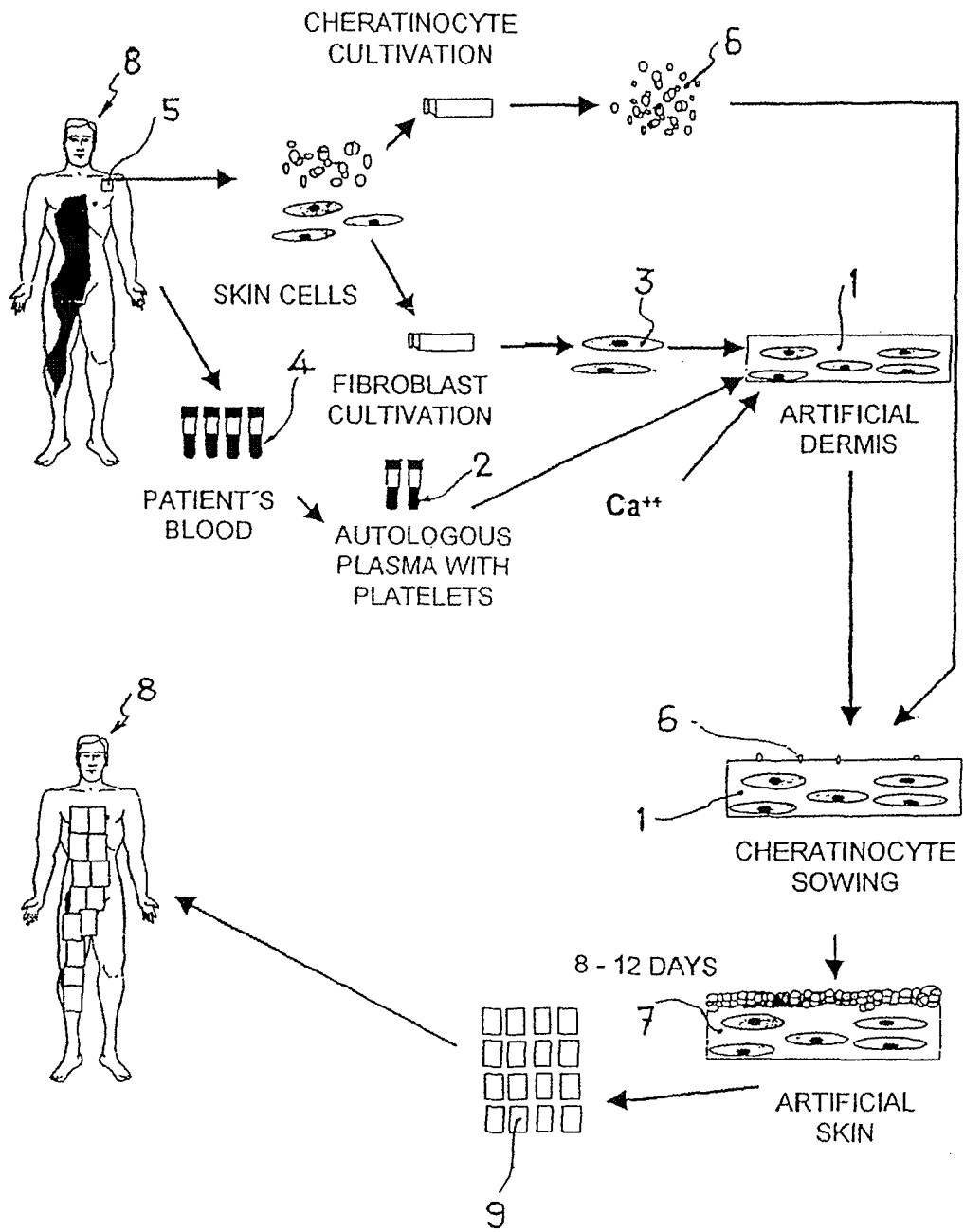

ARTIFICIAL DERMIS AND METHOD OF PREPARATION

RELATED APPLICATION INFORMATION

The present application is a continuation application of U.S. patent application Ser. No. 11/809,665 filed on May 31, 2007 now abandoned, which is a continuation of application Ser. No. 10/469,554 filed on Apr. 9, 2004 (U.S. Pat. No. 7,244,552 Issued Jul. 17, 2007) which is a 371 of International Application PCT/ES2002/000087 filed on Feb. 28, 2002 and entitled "ARTIFICIAL DERMIS AND METHOD OF PREPARATION", which was published in the English language on 19 Sep. 2002, with International Publication Number WO 2002/072800 A1, and which claims priority from Spanish Patent Application P200100494, filed 1 Mar. 2001.

PURPOSE AND FIELD OF APPLICATION

This invention refers to an artificial dermis made by plasma clotted in the presence of platelets, by adding calcium, and in which fibroblasts or other dermal cells are embedded. In turn, Keratinocytes can be seed on the surface of this artificial dermis, which makes it especially useful for the treatment of major burns, chronic ulcers, tests controlling sensitivity to different products, etc. By using genetically altered cells, it can be used as a vehicle for gene therapy.

BACKGROUND OF THE INVENTION

The skin is a tissue made up of two parts, the epithelium or external part and the dermis, or the internal part on which the epithelium is positioned. These two parts have clearly different characteristics. There is practically no extracellular tissue in the epidermis, whereas this component is clearly predominant over cells in the dermis. The skin is a tissue that can be re-constructed by tissue engineering techniques (Parenteau N, Sci Am, 280: 83-84, 1999). In these techniques, in general, the cellular component is generated "ex vivo" by cell cultivation techniques. These techniques, starting with a small number of cells taken from a small skin biopsy, obtain a large number of cells in a short time. These "ex vivo" expanded cells can be used to build large areas of artificial skin. The extracellular matrix can not be produced by cell cultivation, but it is previously designed and manufactured outside the body. The extracellular matrix has to be capable of providing structures that facilitate the adhesion of the previously cultivated dermal cells and stimulating the normal growth of these cells. On this artificial matrix, the cells begin to manufacture the normal proteins that make up the natural dermal matrix, and at the same time, they slowly degrade the original structure, so that over time this artificial matrix is replaced by a true extracellular matrix completely similar to a natural one. The previously cultivated epithelial cells (Keratinocytes in the case of skin) can be seeded on this artificial matrix, where with new cell cultivation techniques, these cells are capable of generating a structure that is very similar to the normal epithelium from which they originated. In other words, one of the key factors in skin tissue engineering is the design of dermal matrices that imitate the body's natural conditions as much as possible, and where the cells introduced are capable of starting a complex process, the purpose of which is to develop a structure as similar as possible to natural skin. The other key factor in skin tissue engineering is the capacity of the dermal matrix to facilitate the growth of the cells that are seeded on it. The development of dermal matrices that encourage the growth of both dermal and epidermal cells would mean that it would be possible to cultivate large areas of artificial skin from a minor biopsy. This is especially important when the artificial skin is for treating major burns, where up to 90-95% of the body's total surface area has to be replaced as quickly as possible, using the small areas of health skin that remain on the patient. The lack of dermal matrices capable of generating these large areas of artificial skin from minor biopsies is one of the limitations of previously described dermal matrices (Sheridan R and Tompkins, Burns 25: 97-103, 1999).

There are several artificial dermis models. Some of the previously used models are described briefly below:

Collagen type I of animal origin, since this is the most abundant of the proteins present in the dermis (Maraguchi T et al. Plast Reconstr Surg, 93: 537-544, 1994, Muhart et al. Arch Dermatol, 135: 913-918, 1999).

Chondroitin sulphate (Boyce S et al. Surgery, 103: 421-431, 1988).

Nylon associated or not to an impermeable Sylastic membrane (Naughton and Mansbridge, Clin Plast Surg, 26: 579-586, 1999).

Poly-lactide/poly-glycolide (Giardino et al, J Trauma 47: 303-308, 1999). These polymers form a web that acts as a structure where the fibroblasts take, grow and are capable of segregating normal dermal matrix proteins.

Fibrin. This protein, the precursor of which, fibrinogen, is obtained from human plasma, has been used in different ways in the cultivation of keratinocytes. Fibrin provides a good base for the growth of epithelial cells, so this protein has been used as an inert support on which to grow cheratinocytes (Ronfard et al, Burns 17: 181-184, 1991) (Broly et al, ES2060803). Fibrin does not interfere with the later development of a correct dermal/epidermal binding between the bed of the injury and the cultivated keratinocytes. Because of these characteristics, fibrin has been broadly used as a transport system for keratinocytes (Pellegrino et al. Transplantation 68: 868-879, 1999, Kaiser and Stark, Burns 20: 23-29, 1994).

Fibrin and/or the gels made after the clotting of human plasma proteins have been used as a vehicle for transplanting skin cells previously expanded "in vitro" (Sadaki I, JP10277143).

Fibrin can also be used as a dermal base for the production of large areas of cultivated skin (Meana et al, Burns 24: 621-630, 1998). The fibroblasts embedded in fibrin gels are capable of growing. At the same time, these fibroblasts act like authentic inducers of keratinocyte growth, so that platting a very limited number of cultivated keratinocytes on a gel made up of fibrin and fibroblasts, in 8-12 days we obtain a stratified confluent epithelium that imitates the normal human epithelium. This capacity of fibrin gels for the development of epithelial cells has been used in another artificial skin model (Meana et al, P9701533). Moreover, fibrin can be used in the presence of other components that increase its rigidity and facilitate its use as a dermal support (Meana A. P9601684). This capacity of fibrin gels and fibroblasts to obtain large areas of artificial skin from a minor skin biopsy is lacking in models based on artificial dermis with other compositions. The explanation of this lies in the fact that fibrin-based gels are able to imitate the physiological wound-repairing mechanism (Martin P, Science 276: 75-81, 1997).

However, the production of the dermal matrix based on fibrin concentrates is only an imitation of the physiological process. The true fibrin clot that is formed as part of the tissue repair and defence mechanism is at the expense of blood plasma. There are many proteins in the extracellular blood fraction, and one of them, fibrinogen, is the soluble precursor of fibrin, the main but not the only protein in the clot. The leak of the plasma after the aggression of a tissue is one of the ways in which the entire clotting process is started. When the aggression occurs and the tissue products come into contact with the skin, the so-called extrinsic clotting pathway is activated, and the final result if the activation of the inactive thrombin precursor present in plasma. This thrombin starts converting the fibrinogen into fibrin and eventually into soluble fibrin which, bound to blood cells, forms part of the fibrin clot, the first step in curing and later repairing a lesion to the body (Singer and Clark, N Engl J med. 341: 736-746, 1999). Of the cells involved in forming the clot, special mention should be made of the platelets. These cells are an important deposit for cytokines, the substances responsible for initiating the cell response in the final repair process for wounds. Platelets are also involved in the development of the fibrin clot inside the veins. This is called the intrinsic clotting pathway, in which a stimulus provokes the development of platelet aggregation that will activate a series of plasmatic proteins that, in turn, will stimulate others by a cascade process mechanism. Finally, we will have the thrombin that will start forming the clot. In both processes, extrinsic and intrinsic clotting pathways, the presence of free calcium ions is essential to complete their development, because some of these pathways' proteins depend on this ion to be activated. After the fibrin clot is formed from the blood plasma, the cytokines, initially released by the platelets, will attract other cells, such as macrophages, neutrophyls, etc., which will start to destroy the clot and replace this fibrinoid tissue by the normal tissue that existed prior to the aggression. These cells, in turn, will manufacture other cytokines that will maintain and control the response to the aggression. They will attract dermal fibroblasts and endothelial cells to the wound, which will complete the repair response. These new repairing cells will manufacture other cytokines that will attract epithelial cells to the wound to cover its entire surface. In turn, epithelial cells are capable of manufacturing many substances that provoke different cell responses in the underlying dermal cells. Epithelial cells also have a catabolic effect on the fibrin clot, because they need to penetrate and eliminate it in order to re-coat the surface of the wound (Singer and Clark, N Eng J. Med. 341: 738-746, 1999). Once the lesion has been covered by the epithelium, the curing process is complete.

We can consider that the physiological repair of a wound is based on a fibrin clot rich in plasmatic cytokines, based on the fibrinogen dissolved in the plasma. This clot will start the body's primary repair response and will induce the nearby epithelial cells to migrate from the points closest to the wound and finally close it. This repair process has limits, and when the injury completely destroys all the epithelial cells present (broad and deep burns), an amount of artificial epithelium is required, either by means of grafts of cultivated keratinocytes, suspended keratinocytes or cultivated artificial skin, for the process to be completed (Naysaria et al. TIBTECH 13: 91-100, 1995).

If the origin of wound repair is in the fibrin clot from plasma, it is possible for an artificial skin model based on the use of human plasma as the primary source of the extracellular matrix to be highly effective and provide extraordinary encouragement for cell growth, since it reconstructs the physiological conditions of the body's wound repair process.

DESCRIPTION OF THE INVENTION

This invention describes the development of an artificial dermis based on the use of human plasma as the fundamental basis for the extracellular matrix. This human plasma is obtained by primary fractionating of total blood, and includes platelets in its composition. The previously cultivated dermal fibroblasts are re-suspended in the plasma, and after clotting this produces an artificial dermis. The "ex vivo" expanded keratinocytes will later be seeded on this artificial dermis. On this artificial dermis, the keratinocytes show a similar behaviour "in vitro" as in "in vivo" in the wound repair process. They adhere, migrate and grow in such a way that, from just a few cells, in 8-12 days they cover the entire surface of the plasma gel and form a stratified epithelium. The final result is that from a small initial number of cells, days later we obtain a tissue composed of two parts, one upper part of stratified epithelial cells and one lower part consisting of an extracellular matrix densely populated with fibroblasts.

These gels can be prepared for transplantation using the previously described technique (Meana et al, P9701533) and fixing them to a solid support, so that they can potentially be used to treat skin injuries. Using a larger than normal amount of gel, these gels can be used without fixing to a solid support, which reduces their handling difficulties even further and decreases the final cost. The transplantation of this artificial skin in experimental animals shows that it is capable of taking when placed on a wound, and that it also develops all the layers normally seen in mature human skin, including the stratum corneum. The studies conducted to date also show that the epithelisation lasts for the entire animal's life-span. These experimental results imply that this artificial skin can be used in the definitive epithelisation of patients with burns.

The accessibility of the material employed in this dermis, and its simple manipulation, implies an important reduction of the final cost of the product, which has been one of the factors that has restricted the massive use of cultivated skin in therapy (Philips T J, Arch Dermatol 135: 977-978, 1999).

The artificial dermis that is the subject of this invention consists of a gel produced by human plasma clotting in the presence of platelets, to which cultivated human fibroblasts have previously been added. The clotting is the result of adding calcium salts. Alternatively, it can be produced by the transformation of the fibrinogen contained in the plasma by exogenous thrombin and $Ca^{++}$ ions.

Depending on the concentration of fibrinogen in the gel, this clotting can take place in the presence or not of agents that act as anti-fibrinolytics, and their addition is recommended when the fibrinogen is less than 2 mg/ml of gel.

The plasma is obtained by light centrifugation of total blood extracted by vein puncturing in the presence of anti-clotting agents, preferably agents that chelate the calcium ion. The plasma can also be extracted by plasmapheresis.

Keratinocytes can later be seeded on this gel based on plasma and cultivated fibroblasts. These cells, platted at a low density on the surface and cultivated for 8-12 days, in the presence of one of the different media that are used to grow keratinocytes, grow and are capable of forming a stratified epithelium. This skin, consisting of the plasma/fibroblasts gel and the autologous cultivated epithelium, could be used in the definitive epithelisation of major burn patients. It could also be used with a donor's epithelium as a temporary coverage for burns, or as therapy for chronic skin ulcers. This cultivation system can also be applied to other human epitheliums other than skin, generating other epithelial tissues such as oral mucosa, vesicular mucosa, etc.

This prototype could be transplanted to a wound, take and epithelise the injury.

This type of gel may need to be fixed to a solid support to enable it to be used for transplantation. This support could be a gauze, steeped in vaselin or not. The gauze can be fixed to the gel by an inert inorganic glue of clinical use or another mechanical system. A silicone membrane can also be used as a support, in which case it could be fixed by an organic glue such as fibrin. In the latter conditions, this kind of gel can be used without a keratinocyte layer to temporarily cover skin injuries, providing them with a dermal base.

The advantages of human plasma and fibroblast gels are as follows:

- The raw material is easy to obtain. The plasma is produced from total human blood extracted by vein puncturing, normally in the presence of a chelating calcium. Only centrifugation is required to obtain plasma from total blood. Human plasma can also be obtained from total blood using the apheresis procedure.
- They ensure rapid keratinocyte growth. The fibroblasts grow rapidly inside the plasma gel and they are capable of increasing keratinocyte growth, even when the fibroblasts are at an extremely low concentration initially. In plasma and fibroblast gels, these cells grow secreting substances that makes them authentic feeder cells, stimulating and controlling keratinocyte growth. With the cultivation of keratinocytes on this type of gel, it is possible to produce a greater total area of cultivated skin than by using the methods described to date, just 3 to 4 weeks after performing a biopsy.
- The gel does not retract or reduce its surface area and total volume in the first 30 days of growth.
- The possibility of replacing the dermal fibroblasts by cells of another origin. In the gels made from plasma, the function of the fibroblasts can be replaced by other cells. The mesenchyme stem cells that are found in bone marrow (Young et al. J Ortho Res 16: 406-413, 1996) can act like fibroblasts when they are embedded in these gels. Other cells that can also increase keratinocyte growth are endothelial cells. The use of dermal cells from different regions other than the skin is a new alternative, particularly for major burn patients, where the availability of skin to start cell growth is seriously limited.
- The possibility of starting the clotting without adding an exogenous starter protein (bovine or human thrombin). Human plasma, unlike fibrinogen concentrates, has all the components of the clotting cascade, including the thrombin that is present in the form of its precursor (inactive), prothrombin. The clotting, and therefore the production of the artificial dermis, can be performed using exclusively the intrinsic pathway, by the addition of calcium and in presence of phospholipids of platelet origin (also present, as mentioned in the following section). The use of this pathway for clotting means that there is no need for exogenous thrombin, which is required when working with fibrinogen concentrated. By the use of plasma in the presence of platelets, it is now possible, for the first time, for the origin of all the proteins in the artificial dermis to come from the patients to which the dermis will eventually be transplanted.
- The enrichment of growth factors of platelet origin.

In the gel produced by direct plasma clotting are present part of the growth factors and cellular adhesion molecules that are also present in fibrin gels. However, in gels produced by direct plasma clotting plasma, platelet cytokines are also present, since a fraction of these cells is always present after centrifugation. We can also enrich the platelet fraction of the plasma by modifying the centrifugation parameters. The presence of platelets makes our dermis very rich in PDGF and TGF-B (Anitua E, Int Oral Maxillofac Implants 14: 529-535, 1999), both key factors in starting tissue repair (Marx et al, Oral Surg Oral Med Oral Pathol Oral Radiol Endod, 85: 638-646, 1998). All this means that the gels produced from human plasma and platelets and populated with fibroblasts, preserve and increase the capacity of fibrin gels to obtain large areas of cultivated artificial skin in a relatively short time, which makes them suitable for keratinocyte cultivation to treat major burn patients. The cell growth both of the fibroblasts inside the fibrin and the keratinocytes seeded on the surface, is so important that it is possible to obtain sufficient cells for both the dermal and the epidermal component, from a minor biopsy. In other words, the cellular component of our artificial skin comes exclusively from the patient to whom it will later be transplanted.

With the use of plasma, it is possible to produce stable gels at a very low fibrinogen concentration. The fibrinogen concentration required for the gel to maintain its integrity throughout the culture can be less than 0.5 mg per thousand. Even at these concentrations, the gels made from plasma are stable, and they are not rapidly digested by the fibroblasts and keratinocytes seeded on them. Moreover, if they are associated to an anti-fibrinolytic product (aprotinin, tranexamic acid, epsylon-aminocaproic acid), the fibrinogen concentration can be even lower, so that from 2-3 ml of plasma, we can obtain up to 70-90 cm$^2$ of skin. The total plasma concentration could be reduced still further by associating the plasma gel to a solid stand (vicryl, polactic-polyglycolic acid, etc.). Another advantage of these gels (since there are minimal amounts of plasma per cm2 of gel) is that it is possible for the plasma used in the artificial dermis to come from the patient him/herself. The use of plasma from the patient him/herself, together with the absence of exogenous proteins in the dermis, plus the possibility of all the cells in the artificial skin coming from the own patient, is one of the new aspects of this invention, since it is possible, for the first time, to treat large burnt areas with artificial skin in which all the components come from the own patient, that is the treatment of major burn patients with whole autologous artificial skin.

Due to their biological characteristics, these gels can be used as a support for cells (fibroblasts or other cell species, including genetically altered cells, capable of producing proteins (endothelial growth factors, etc.) that are useful in different diseases.

BRIEF DESCRIPTION OF THE FIGURES

FIG. 1 shows a diagram of the operations required for the transplantation of skin to a major burn patient using the artificial dermis that is the subject of this invention.

DETAILED DESCRIPTION OF THE INVENTION

Following is a description of how to obtain the main components of the dermal base.

The plasma with platelets (2) is obtained from total blood (4). This is extracted by vein puncturing in the presence of an anti-clotting agent of clinical use, particularly an anti-clotting agent that acts by means of the chelation of the ionised $Ca^{++}$ concentration in total blood. The total blood (4) can be obtained in one of the bags normally used in haemotherapy or, for small amounts, from blood collected in small containers of the Vacutainer® type. The plasma with platelets (2) will be obtained by centrifugation at low speed to obtain a plasma very rich in platelets, or at high speed to obtain a product with a lower concentration of these cells. Once the blood has been centrifuged, the corresponding plasma fraction will be used directly to form the gel or be frozen at −20° C. for later use.

Before being stored, the plasma can also be treated with methylene blue to inactivate possible viruses if the plasma is not to be used in an autologous manner (obtained from the patient to be treated)

The gel is made from the fibrinogen present in the plasma, either by the action of human or bovine thrombin and calcium ions, or exclusively using the prothrombin that is present in the plasma itself, by adding calcium, preferably in the form of calcium chloride to reconstitute the ionic calcium values that are spontaneously present in the plasma and which had been nullified by the sodium citrate of EDTA used as anti-clotting agents. Fibrin is the main structural component in the gel, but not the only one, because in this model fibrin is covalently bound to the plasmatic fibronectin. It is also important to point out that there are many other proteins in human plasma, albumin, globulins, growth factors, plasminogen, etc., which are involved in the gel's production and stability and in the growth of the cells that are cultivated in the gel.

Human fibroblasts from several sources can be used:
1) Homologous fibroblasts. Cultivated from foreskins obtained from phimosis operations and/or dermal fibroblasts from healthy adults. The patient or his/her legal representatives have to provide their consent.
2) Autologous fibroblasts. Obtained from a skin biopsy (5) extracted from a patient (8), which will be used exclusively in the dermis to be implanted to the same patient.

The gel is obtained as follows:
On the one hand, the fibroblasts are re-suspended in a culture medium or a 0.9% sodium chloride solution. The volume of plasma is added to this solution, followed by the anti-fibrinolytic agent. When this solution is ready, it is clotted in 2 different ways:
1) Adding a 1% calcium chloride solution dissolved in 0.9% sodium chloride.
2) Adding a thrombin (between 2 and 4 units) solution dissolved in 40 mM calcium chloride.

The first method uses the clotting factors present in the plasma, which are activated by the presence of Ca. This is a slow process that will eventually transform the prothrombin present in the plasma into thrombin. This protein will then act on the fibrinogen, transforming it into fibrin, and eventually, by the action of other clotting factors, into insoluble fibrin, the main structural protein in our dermis.

The second alternative is to directly add the thrombin to the plasma, which speeds the process up a great deal. In counterpart, another protein of human or bovine origin is added to the product, with the consequent problems related to the possible transmission of diseases.

The mixture is introduced into a cell culture dish and left for 30-120 minutes at 37° C. until the gel has formed completely. At the end of this time, the gel has become solid, and can be covered with a complete culture medium.

The gels produced are stored for 14 days at most at 37° C. in a 5% $CO_2$ incubator until they are used for cultivated keratinocytes. In normal cultivation conditions, these gels remain stable and adhered to the bottom of the dish, and no retraction or loss of volume is observed.

If what is required is a complete skin (7) growth, the keratinocytes (6) obtained from a primary culture will be added to this dermal base. These cells can be cultivated in very different ways, in the presence of feeder cells, using media low in calcium or completely defined media (Myers at al, Am J Surg 170: 75-83, 1995). The keratinocytes (6) produced with any of these systems can be used on this artificial dermis (1).

Once the keratinocytes seeded are preconfluent or completely confluent, the gels are ready for clinical use and they are prepared for transplantation. This can be done by fixing them to a support that will make it possible to transport the gel without losing any or breakage to the site of the transplant. This fixing process will not be required for very thick gels. In general, when a large area of keratinocyte growth is required in a short time (major burn patients), small gels will be used, requiring a solid support (9) for transplantation. The cultures for other uses (chronic ulcers) can be handled and transplanted without this fixing process. The gels will be fixed to this solid support using an inorganic glue of clinical use, and applying minimal sutures. Once the culture is fixed to the support, it is separated from the bottom of the dish by hand.

As a source of plasma with platelets (2), we use total human blood (4) extracted by vein puncturing in the presence of anti-clotting agents.

If what is required is to obtain large amounts of plasma from a single donor, the extraction will be made using a 450 ml blood extraction bag containing an anti-clotting/preservative solution (SAG-Manitol), normally what is called a triple bag set. Once extracted, the total blood is centrifuged. If we need a plasma rich in platelets (PRP), centrifugation will be approximately 1500 rpm for 5 minutes at 20° C.). If we need a plasma less rich in platelets (PPP), centrifugation will be at approximately 2900-300 rpm for 10 minutes). After centrifugation, the resulting plasma is separated by normal fractionating of the blood bag. The plasma obtained can be used directly, making it virally inactive by treating with methylene blue. This plasma can be preserved for at least a year at −20° C.

If what is required is small amounts of plasma for small dermis areas, the total blood extraction will be performed with sterile vacuum tubes (of the Vacutainer® type) or other models of similar characteristics, using a calcium chelator in saturated conditions (sodium citrate, EDTA) in the proportions recommended by the manufacturer, as an anti-clotting solution. Another kind of anti-clotting agent, sodium heparin, can also be used. Depending on whether PRP or PPP is required, centrifugation will take place at 160 g (PRP) or 400 g (PPP) for 10 minutes. The plasma fraction with platelets (2) is removed from the tube; attempting not to remove the red blood cells. To increase the plasma extraction yield, the pellet containing the rest of the cell fraction is then centrifuged at 3000 g for 10 minutes. At the end of this operation, the plasma is removed and mixed with the supernatant obtained from the previous centrifugation. Since this culture system will normally be used in the production of dermis to be transplanted to the patient providing the blood (autologous plasma), methylene blue treatment is not necessary.

Whichever method is chosen to obtain the total blood and separate the plasma, the fibrinogen dissolved in the plasma will be measured by a commercial method derived from the method initially described by Kraus (Multifibren® U, Dade Behring).

Different lines of human fibroblasts (3) will be obtained from human foreskins obtained after programmed phimosis surgery or from a skin biopsy (5). The sample is collected in a transport medium (DMEM, 10% bovine foetal serum, 100 u/ml penicillin, 100 µg/ml streptomycin). In the laboratory, it is washed three times in sterile PBS and carefully cut into pieces. It is introduced into 30 ml of 0.05% tripsin-0.02% EDTA solution while stirring at 37° C. Every 30 minutes, the tripsin is collected and changed for fresh tripsin. The tripsin is neutralised by adding complete culture medium (DMEN, 10% bovine foetal serum). The operation is repeated until no more cells are obtained. The cells obtained are placed in a culture dish at a density of 100,000 cells per $cm^2$ of culture surface. The medium is changed every 72 hours until the cells are confluent. Upon confluence, these cells are tripsinated and secondary cultures are made in a proportion of two culture dishes for each culture dish in the previous phase. When the cells show a single layer of cells similar to the fibroblasts (3) part of them are frozen, using a common technique, and they are stored in cryovials in liquid nitrogen. The ideal passes for the use of these fibroblasts are between the $4^{th}$ and the $12^{th}$.

When human fibroblasts (3) from the same patient (8) are going to be used in the artificial dermis (1), we proceed in the same way. The patient's (8) skin biopsy (5) will be processed as described in the previous section. Once the cells are obtained, part of them will be cultivated in DMEM 10% bovine foetal serum at a density of 100,000 cells per $cm^2$. The corresponding sub-cultures will be prepared until we obtain a sufficient number of human fibroblasts (3) to manufacture the artificial dermis (1) that the patient (8) needs.

The cultivated human fibroblasts (3) are tripsinated, counted and re-suspended in culture medium for immediate use in the artificial dermis (1).

Once the basic materials are obtained, we proceed to manufacture the gel.

The calculation provided in as used in the manufacture of a dermal base sufficient for a 75 $cm^2$ culture dish. For other dimensions, the same values will be used, reducing or increasing them in proportion to the surface of the culture dish.

Preparation of the Artificial Dermis (1):

A solution is prepared containing basically culture medium, 0.9% sodium chloride solution and human fibroblasts (3) (between 30,000 and 250,000 cells). If necessary, the anti-fibrinolytic (10,000 U of aprotinin, between 5 and 20 mg of tranexamic acid or 200-300 mg of epsylon-aminocaproic acid) is added, and finally, 1 ml of 0.04 M $Cl_2Ca$ solution, in which between 2 and 4 IU of thrombin have previously been dissolved. When these components have been mixed, we add between 3 and 6 ml of plasma with platelets (2) (depending on the fibrinogen concentration). The final volume is completed to 15 ml with more or less sodium chloride, depending on the amount of plasma used. The solution is rapidly introduced into the culture dish, and distributed homogeneously over its surface. The dish is left in a $CO_2$ oven at 37° until the clotting occurs and the gel is polymerised.

As an alternative to the use of exogenous thrombin, the gel can be prepared as follows:

A solution is prepared containing basically culture medium, 0.9% sodium chloride solution and human fibroblasts (3) (between 30,000 and 250,000 cells). If necessary, the anti-fibrinolytic (10,000 U of aprotinin, between 5 and 20 mg of tranexamic acid or 200-800 mg of epsylon-aminocaproic acid) is added, and finally 1 ml of 1% $Cl_2Ca$ solution dissolved in 0.9% sodium chloride. Once these components have been mixed, the human plasma with platelets (2) is added. The final volume is completed to 15 ml with more or less sodium chloride, depending on the amount of plasma used. The solution is rapidly introduces into the culture dish and spread homogeneously over the surface. The dish is left in a $CO_2$ oven at 37° until clotting occurs and the gel is polymerised. With this method, the gel polymerises very slowly.

The approximate final concentration of fibrinogen in the gel is between 0.4 and 2 mg of fibrinogen/ml of gel. Although the plasma can be used in some conditions without being previously diluted with sodium chloride, so the fibrinogen concentration could be as much as 4 mg/ml of gel.

The initial concentration of human fibroblasts (3) in the gel can vary considerably. In general, a concentration of no less than 500 fibroblasts/$cm^2$ of gel surface is recommended, although it can be greater. An initial number of fibroblasts of over 4,000/$cm^2$ is not recommended, because with higher concentrations the gels tend to be digested by the $6^{th}$-$7^{th}$ day of growth, and can not be processed for transplantation.

The keratinocytes are seeded on this gel at an extremely varied density (between 1,500 and 15,000 cells/$cm^2$ of dermis), depending on the amount of growth required.

The keratinocytes (6) employed can be obtained from a primary culture from a skin biopsy (5). The cultivation of keratinocytes (6) on this gel can be done by any of the cheratinocyte cultivation systems described above, although the best results have been obtained with media supplemented with bovine foetal serum.

When the keratinocytes are confluent or preconfluent, normally on the $8^{th}$ day of growth, the sheet is prepared for transplantation. The layer of artificial skin (7) has to be separated from the bottom of the culture dish, either directly or fixed to a solid support. Fixing to a solid support (9) is necessary when the gels are not very consistent (initial concentration low in fibrinogen, large areas, etc.), which means that their clinical use would not be possible without fixing them to a solid support. This procedure consists of the following stages:

The last culture medium is removed and the culture dish is opened. The gel is covered with a sterile gauze (vaselin-coated or not), so that the gauze exactly covers the entire gel surface. A scalpel is used to separate the sides of the gel from the culture dish. Once this manoeuvre has been completed, it will be fixed to the upper surface of the gel (the side where the cheratinocytes are) by the use of an inorganic glue (Cyanoacrylate, Histoacryl®, Braum or another of similar characteristics). The cyanoacrylate will be used applying small drops to the edges of the gel and different drops of glue can be applied to the centre. Once the glue is dry, a spatula is used to separate the gel from the culture dish. The gauze helps to maintain the gel containing the dermal base and the upper layer of cultivated cheratinocytes in one piece. This prototype can then be transported, without losing its integrity or breaking, for over 16 hours.

Table 1 compares the basic characteristics of the previous technique and the artificial dermis that is the subject of this invention.

TABLE 1

|  | PREVIOUS TECHNIQUE (Sadaki) | INVENTION |
|---|---|---|
| Platelets | NO | YES |
| Thrombin | YES | NOT COMPULSORY |
| Fibrinogen | 60 mg/ml | 0.5-2 mg/ml |
| Fibroblasts | 50,000/cm2 | <4,000/cm2 |
| Gel cultivation time | 22 h | 8 to 12 days |
| Cellular growth in the gel | MINIMAL | YES |
| Keratinocytes | 50,000/cm2 | 1,500-15,000/cm2 |
| Biopsy size | X 83 | X 1000-5000 |

What is claimed:

1. An artificial skin comprising a matrix obtained by clotting human plasma-containing platelets and dermal cells, wherein platelets and dermal cells are embedded in the matrix, said artificial skin further comprising cultivated keratinocytes on a surface of the matrix, and wherein the artificial skin is suitable for transplantation.

2. The artificial skin according to claim 1, wherein the plasma has undergone viral inactivation.

3. The artificial skin according to claim 1, wherein the matrix further comprises a biocompatible polymer.

4. The artificial skin according to claim 1, wherein the dermal cells are fibroblasts.

5. An artificial skin comprising a matrix obtained by clotting human plasma containing platelets and dermal cells, wherein platelets and dermal cells are embedded in the matrix, said artificial skin further comprising cultivated keratinocytes on a surface of the matrix, wherein the artificial skin is suitable for transplantation, and, wherein the dermal cells are mesenchymal stem cells or endothelial cells.

6. A method of obtaining artificial skin, comprising the steps of:
   a) centrifuging whole blood obtained from a donor at low speed to obtain plasma containing platelets;
   b) subsequently freezing the plasma,
   c) culturing dermal cells from a skin biopsy,
   d) de-frosting the frozen plasma;
   e) clotting the previously de-frosted plasma containing platelets, by adding calcium salts, to obtain a fibrin matrix, and
   f) embedding dermal cells inside the fibrin matrix.

7. Method according to claim 6, wherein thrombin is added during the clotting.

8. Method according to claim 7, wherein the thrombin is added in a concentration 0.2 IU/ml.

9. Method according to claim 6, wherein said calcium salts in step (e) consist of 1% $CaCl_2$ in a solution and are added at a ratio of 1 ml for every 3 to 6 ml of plasma containing platelets.

\* \* \* \* \*